(12) United States Patent
Leach

(10) Patent No.: US 7,077,339 B2
(45) Date of Patent: Jul. 18, 2006

(54) SPRAY APPLICATOR

(75) Inventor: Michael D Leach, Warsaw, IN (US)

(73) Assignee: Biomet, Inc., Warsaw, IN (US)

( * ) Notice: Subject to any disclaimer, the term of this patent is extended or adjusted under 35 U.S.C. 154(b) by 220 days.

(21) Appl. No.: 10/357,056

(22) Filed: Feb. 3, 2003

(65) Prior Publication Data
US 2004/0159715 A1 Aug. 19, 2004

(51) Int. Cl.
B05B 7/12 (2006.01)

(52) U.S. Cl. .............. 239/417; 239/418; 239/417.5; 222/137; 222/327; 222/145.5; 604/191

(58) Field of Classification Search .............. 239/409, 239/417, 418, 416.3, 417.5; 222/129, 137, 222/145, 327; 604/83, 191
See application file for complete search history.

(56) References Cited

U.S. PATENT DOCUMENTS

| | | |
|---|---|---|
| 1,948,388 A | 2/1934 | Liberson |
| 1,950,137 A | 3/1934 | Dowe |
| 2,112,160 A | 3/1938 | Johnson |
| 2,322,753 A | 6/1943 | Thomas |
| 3,223,083 A | 12/1965 | Cobey |
| 3,236,418 A | 2/1966 | Dalle et al. |
| 3,467,096 A | 9/1969 | Horn |
| 3,552,394 A | 1/1971 | Horn |
| 3,767,085 A | 10/1973 | Cannon et al. |
| 3,828,980 A | 8/1974 | Creighton et al. |
| 4,040,420 A | 8/1977 | Speer |
| 4,121,739 A | 10/1978 | Devaney et al. |
| 4,226,235 A | 10/1980 | Sarnoff et al. |
| 4,260,077 A | 4/1981 | Schroeder |
| 4,359,049 A | 11/1982 | Redl et al. |
| 4,434,820 A | 3/1984 | Glass |
| 4,465,476 A | 8/1984 | Gahwiler |
| 4,631,055 A * | 12/1986 | Redl et al. ............ 604/82 |
| 4,673,395 A | 6/1987 | Phillips |
| 4,734,261 A | 3/1988 | Koizumi et al. |
| 4,735,616 A | 4/1988 | Eibl et al. |
| 4,826,048 A | 5/1989 | Skorka et al. |
| 4,874,368 A | 10/1989 | Miller et al. |
| 4,902,281 A | 2/1990 | Avoy |
| 4,978,336 A | 12/1990 | Capozzi et al. |
| 4,979,942 A * | 12/1990 | Wolf et al. ............ 604/83 |
| 5,049,135 A | 9/1991 | Davis |
| 5,104,375 A | 4/1992 | Wolf et al. |

(Continued)

FOREIGN PATENT DOCUMENTS

CA 2051638 2/1991

(Continued)

OTHER PUBLICATIONS

Merit Medical, OEM Products Catalog 3 pages.

*Primary Examiner*—Dinh Q. Nguyen
(74) *Attorney, Agent, or Firm*—Harness, Dickey & Pierce, P.L.C.

(57) ABSTRACT

An applicator for applying a multi-component bio-material including at least two containers. Both containers are held in a structure or oriented in a structure such that material contained in the containers can be expressed from oriented outlets simultaneously. The applicator includes a graspable member which allows the material to be expressed from all containers of the applicator substantially simultaneously. The applicator may be constructed such that a pre-selected and substantially different volume is expressed from each of the containers substantially simultaneously.

33 Claims, 4 Drawing Sheets

U.S. PATENT DOCUMENTS

| | | |
|---|---|---|
| 5,104,387 A | 4/1992 | Pokorney et al. |
| 5,116,315 A | 5/1992 | Capozzi et al. |
| 5,147,323 A | 9/1992 | Haber et al. |
| 5,176,658 A | 1/1993 | Ranford |
| 5,226,887 A | 7/1993 | Farr et al. |
| 5,253,785 A | 10/1993 | Haber et al. |
| 5,290,259 A | 3/1994 | Fischer |
| 5,298,024 A | 3/1994 | Richmond |
| 5,368,563 A | 11/1994 | Lonneman et al. |
| 5,376,079 A | 12/1994 | Holm |
| 5,409,465 A | 4/1995 | Boggs et al. |
| 5,419,491 A | 5/1995 | Breitsprecher |
| 5,445,614 A | 8/1995 | Haber et al. |
| 5,464,396 A | 11/1995 | Barta et al. |
| 5,474,540 A | 12/1995 | Miller et al. |
| 5,505,704 A | 4/1996 | Pawelka et al. |
| 5,520,658 A | 5/1996 | Holm |
| 5,582,596 A | 12/1996 | Fukunaga et al. |
| 5,605,255 A | 2/1997 | Reidel et al. |
| 5,605,541 A | 2/1997 | Holm |
| 5,643,206 A | 7/1997 | Fischer |
| 5,656,035 A | 8/1997 | Avoy |
| 5,665,067 A | 9/1997 | Linder et al. |
| 5,740,965 A | 4/1998 | Miyagi et al. |
| 5,752,626 A | 5/1998 | Bachand |
| 5,759,169 A | 6/1998 | Marx |
| 5,759,171 A | 6/1998 | Coelho et al. |
| 5,810,885 A | 9/1998 | Zinger |
| 5,814,022 A | 9/1998 | Antanavich et al. |
| 5,814,066 A | 9/1998 | Spotnitz |
| 5,935,437 A | 8/1999 | Whitmore |
| 5,951,517 A | 9/1999 | Lampropoulos et al. |
| 5,968,017 A | 10/1999 | Lampropoulos et al. |
| 5,976,102 A | 11/1999 | Epstein |
| 5,980,866 A | 11/1999 | Uchida et al. |
| 5,989,215 A * | 11/1999 | Delmotte et al. ............. 604/82 |
| 6,001,259 A | 12/1999 | Whitmore |
| 6,047,861 A * | 4/2000 | Vidal et al. ................. 222/137 |
| 6,059,749 A | 5/2000 | Marx |
| 6,063,055 A | 5/2000 | Epstein |
| 6,079,868 A | 6/2000 | Rydell |
| 6,099,511 A | 8/2000 | Devos et al. |
| 6,113,571 A | 9/2000 | Zinger et al. |
| 6,132,396 A | 10/2000 | Antanavich et al. |
| 6,206,905 B1 | 3/2001 | Holm et al. |
| 6,234,994 B1 | 5/2001 | Zinger |
| 6,251,370 B1 | 6/2001 | Uchida et al. |
| 6,328,229 B1 | 12/2001 | Duronio et al. |
| 6,331,172 B1 | 12/2001 | Epstein et al. |
| 6,394,982 B1 | 5/2002 | Ehrenfels |
| 6,471,670 B1 | 10/2002 | Enrenfels et al. |
| 6,475,193 B1 | 11/2002 | Park |
| 6,488,650 B1 | 12/2002 | Epstein et al. |
| 6,575,205 B1 * | 6/2003 | Epstein et al. ................. 141/42 |
| 2001/0016709 A1 | 8/2001 | Tovey et al. |

FOREIGN PATENT DOCUMENTS

| | | |
|---|---|---|
| DE | 632579 | 9/1936 |
| DE | 295 16 650 | 1/1996 |
| EP | 0 292 472 B1 | 10/1991 |
| EP | 0 858 776 A2 | 8/1998 |
| FR | 2 661 097 | 10/1991 |
| FR | 2 668 060 | 4/1992 |
| WO | WO 90/01959 | 8/1988 |
| WO | WO 96/39212 | 12/1996 |
| WO | WO 98/02098 | 1/1998 |
| WO | WO 98/10703 | 3/1998 |
| WO | WO 98/10704 | 3/1998 |
| WO | WO 98/13094 | 4/1998 |
| WO | WO 98/40115 | 9/1998 |
| WO | WO99/17833 | 4/1999 |
| WO | WO01/41650 | 6/2001 |

* cited by examiner

SPRAY APPLICATOR

FIELD

The present description relates generally to medical and surgical devices; and particularly to sprayers or applicators of multi-component bio-materials for use during a medical procedure.

BACKGROUND

Many medical and operative procedures require surgically disconnecting various portions of the anatomy. After disconnecting the portions of the anatomy, and to increase recovery from the procedure, it is generally desired to reaffix the disconnected portions. For example, soft tissues can be anchored relative to boney structures or sewn together. Soft tissues may be affixed relative other soft tissues or to a boney structure using various adhesives.

In addition, the surgical wound that is created by opening the epidermis and dermis of a patient can be substantially closed using various techniques. These various techniques include stapling, suturing, and using many adhesives. The adhesives to reaffix the internal soft tissues and the dermis may be substantially similar. Generally, however, the adhesives must be biocompatible so that they are non-toxic to the patient and do not inhibit healing of the wound.

Adhesives may either be entirely manmade, substantially obtained from natural sources, or combinations of both. Regardless of the source, the adhesive may include portions that polymerize or clot (gel) to form the adhesive sealant. Examples of natural adhesives include multi-component or two component biological materials that, when mixed together, form an adhesive that can be used in many applications. For example, a multi-component adhesive may include fibrinogen and thrombin. Various other components, such as particular factors and proteins may be mixed with other biological components to increase efficacy thereof. Fibrinogen and thrombin coagulate to form the adhesive. Adhesives may be used for various applications such as sealing wounds to stop bleeding or increase healing and to minimize infection.

When used in a surgical procedure, it is often desired to supply the materials during the procedure through an efficient and simple to use applicator. It is also desired that the devices be easy to maneuver during the surgical procedure. Also, the devices should ensure a substantially continuous supply of the materials during at least a selected portion of the procedure. It is desirable, however, to also provide an ergonomic design for such an applicator and provide a means for easily re-supplying the applicator once exhausted to ensure a substantially continuous supply of the material to the selected area. It is also desirable to provide a substantially metered amount of the materials so that application of the material can be easily dosed.

For a multi-component adhesive, it may be desirable to apply the adhesive over a substantially large area in a substantially even manner. For example, a multi-component material may be mixed in a mixing apparatus and sprayed onto an external or internal wound to assist in sealing the wound. Regardless an applicator is desired that is easy to fill and maneuver to various areas during a procedure.

SUMMARY

An applicator for a multi-component material includes a first container and a second container with expressing members disposed therein for application of the materials stored in the containers. The containers may define cylinders and include pistons and piston rods as expressing members. Nevertheless, the applicator device is generally designed in an ergonomic and easily manipulated manner to allow ease of use during a selected procedure and increased efficiency by a user.

The applicator generally includes two containers one for receiving each component of a two component material. The applicator, however, may include more than two cylinders to provide for a multi-component material which has more than two components. The applicator device itself may define the cylinders such that the applicator is substantially integral. Alternatively, the applicator may operably interconnect separate cylinders that form the supply containers for the multi-component material.

Extending from each cylinder is an application conduit that may define a cannula to transport the component from the cylinder to an exit port. Associated with the exit ports may be any appropriate applicator attachment. For example, a spray head or nozzle may be affixed to the exit ports such that the multi-component material is expressed from the applicator device as a fine mist onto a selected area.

A graspable member may define a handle or other ergonomically positioned portion to assist a user in grasping the applicator device. The graspable member is operably associated with the various expressing members to allow the user to easily grasp the device and depress the expressing members with a single hand. Therefore, with a single hand, a user may direct and apply selected bio-components to a selected area.

According to an embodiment an applicator for applying a multi-component bio material includes a first container extending along a first axis to selectively contain and disburse a first fluid and a second container extending along a second axis to selectively contain and disburse a second fluid. A container holder operably holds and orients the first container and the second container. A first conduit extends from the first container along the first axis and a second conduit extends from the second container along the second axis. A first outlet further extends from the first conduit while a second outlet extends from the second conduit. The fluid disposed in the first container is expressed through the first outlet while fluid disposed in the second container is expressed through the second outlet.

According to a second embodiment an applicator for applying at least one component of a multi-component bio material includes a first container and a first conduit integrally formed and each extending along a first axis and a second container and a second conduit both extending along a second axis and integrally formed. The first container and the second container are operably fixed relative each other. The first container contains a first material and the second container contains a second material. Both materials may be simultaneously expressed at a selected time.

According to a third embodiment a method for applying a multi-component bio-material to a selected area and at a selected volume with an applicator is described. The applicator includes a containing area for each of the components of the multi-component material. The applicator further includes a conduit acting as an outlet and an inlet for the respective containers. The method includes supplying at least a first material to a first container and a second material to a second container. Supplying the material includes interconnecting a first supply with the first container through a first conduit and interconnecting a second supply with the second container through a second conduit. The first and second containers are filled with the material from the first and second supply. The material may be expressed from the first and second containers selectively simultaneously to a selected area. The material may be selectively supplied at a selected rate from each of the first and second containers.

Further areas of applicability will become apparent from the detailed description provided hereinafter. It should be understood that the detailed description and various examples, while indicating the various embodiments are intended for purposes of illustration only and are not intended to limit the scope of the following claims.

BRIEF DESCRIPTION OF THE DRAWINGS

The present description will become more fully understood from the detailed description and the accompanying drawings, wherein.

DETAILED DESCRIPTION OF VARIOUS EMBODIMENTS

The following description of various embodiments is merely exemplary in nature and is no way intended to limit the scope of the application or uses of the following claims. Moreover, although the following description illustrates and describes a multi-component applicator including two cylinders to receive two components of a multi-component material, it will be understood that more than two cylinders may be provided. It will also be understood that although a "pistol" design is below described and illustrated, that other appropriate designs which allow for ease of use, particularly with one hand, are within the scope of the following description and claims.

Figure 1:
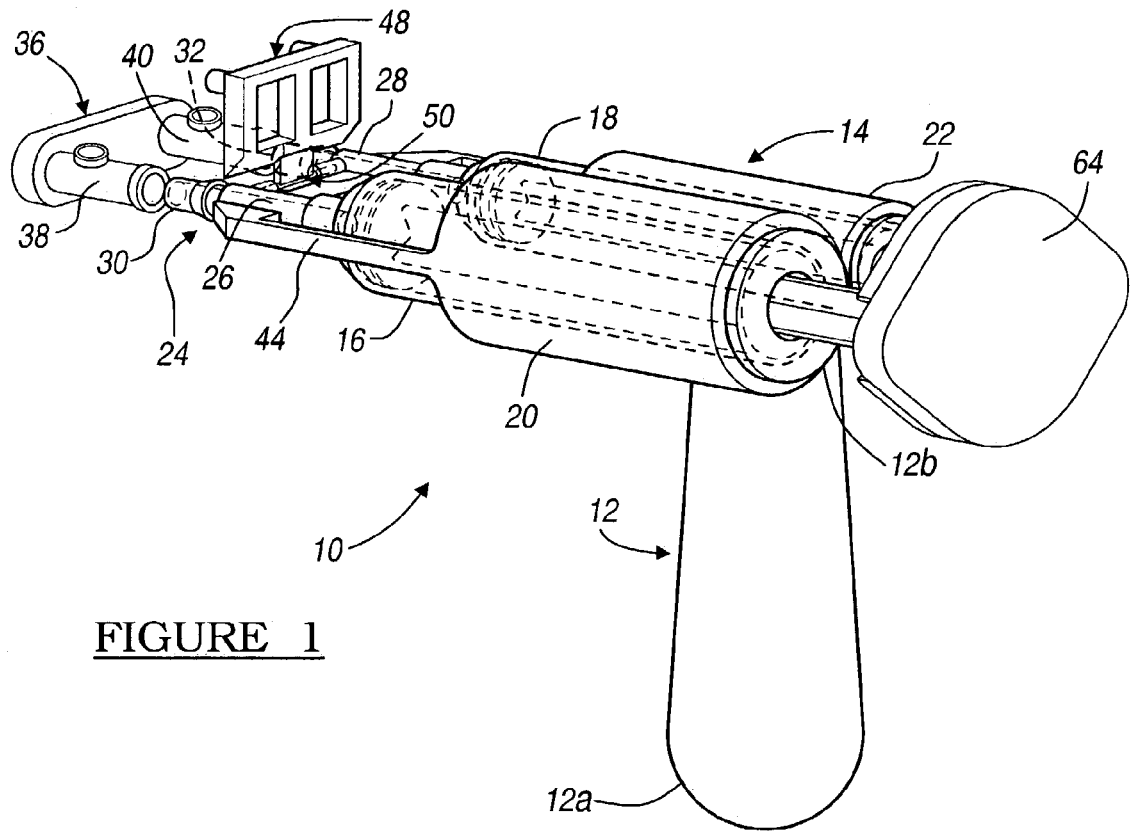
FIG. 1 is a perspective view of an applicator according to an embodiment.

With reference to FIG. 1, a multi-component applicator or spray gun 10 generally includes a handle or graspable member 12, appropriate for grasping with a hand, and a component containment or storage area 14. The handle 12 and component storage area 14 may be integrally formed. It will be understood, however, that the handle 12 need not necessarily be molded to or permanently affixed to the component storage area 14. For example, the handle 12 may include a portion which operably interconnects a mating portion of the component storage area 14 during use. Therefore, before and after use, the handle 12 may be separated from the component storage area 14 for ease of storage or transport. Nevertheless, the handle 12 may be permanently interconnected with the component storage area 14. In this instance, the applicator 10 may be substantially formed as a single member using injection molding or other generally known manufacturing techniques. Alternatively, the applicator 10 may be formed of a metal and forged or cast using generally known manufacturing methods. The applicator 10 may be formed of metal to allow for ease in sterilization in an autoclave or other similar device.

Housed or received within the component storage area 14 is a first container 16 and a second container 18. Although the containers 16 and 18 are illustrated and described as cylinders, it will be understood that the containers may be any appropriate shape. Moreover, the containers 16 and 18 may be preformed or generally known syringes of appropriate volumes and lengths. In this way, syringes of various volumes may be selected to be used with the applicator 10. When a plurality of cylinders are used in the applicator 10, as illustrated in FIG. 1, the cylinders 16 and 18 are received within a respective first holding area or member 20 and a second holding area or member 22. The holding areas 20, 22 and other areas may also be referred to as engaging portions that engage the cylinders 16, 18 to hold them. The cylinder holders 20 and 22 may be formed contacting each other or with a web or support area extending between the cylinder holders 20 and 22. Regardless, the cylinder holding areas 20 and 22 substantially fix the cylinders 16 and 18 relative to each other.

The cylinders 16, 18 are also interconnected with a forward portion or conduit 24 of the applicator 10. Specifically, the first cylinder 16 is connected to a first conduit 26 while the second cylinder 18 is connected to a second conduit 28. Extending from the first conduit 26 is a first outlet 30 while extending from the second conduit 28 is a second outlet 32. The first and second conduits 26, 28 provide a conduit or interconnection between the respective first and second cylinders 16 and 18 to a respective first outlet port 30 and a second outlet port 32. In this way, the conduits 26 and 28 allow the material held within the respective cylinders 16 and 18 to be transported or expressed out the outlets 30 and 32 at a selected time, as described further herein.

The outlets 30 and 32 may be formed in any appropriate manner. For example, the outlets 30 and 32 may include respective outlet holes or bores which spray the material individually from each of the cylinders through the conduits 26 and 28. In addition, the outlets 30 and 32 may be formed to receive an attachment such as a sprayer attachment 36. In a selected embodiment, the outlets 30 and 32 define cones that are adapted to operably engage receiving members 38 and 40 defined by the attachment 36. The interconnection of the outlets 30 and 32 with the receiving portions 38 and 40 provide a substantially liquid tight seal between the attachment 36 and the outlets 30 and 32 such that material pushed out of the cylinders 16 and 18 is expressed through the attachment sprayer 36 during a selected operation. The spray attachment 36, or any other appropriate attachment, may allow mixing of the two components internally to express a mixed material, or externally so the components mix after exiting the pray attachment 36.

The conduits 26 and 28 may be reinforced with reinforcing or support members 44 that extend from the holding members 20 and 22 to support the outlets 30 and 32. The support 44 interconnects the conduits 26 and 28 to provide substantial rigidity to the conduits 26 and 28. The rigidity helps to align the conduits 30 and 32 and further support any attachments required.

In addition, extending either from the supports 44 or the conduits 26 and 28 is a latch member 48. The latch member 48 is interconnected with the supports 44 or conduits 26 and 28 through a hinge mechanism 50. It will be understood, however, that the latch member 48 may be operably interconnected with the applicator 10 through any appropriate mechanism. Nevertheless, the latch member 48 may rotate relative the applicator 10 to engage the spray attachment 36 at a selected time.

Figure 3:
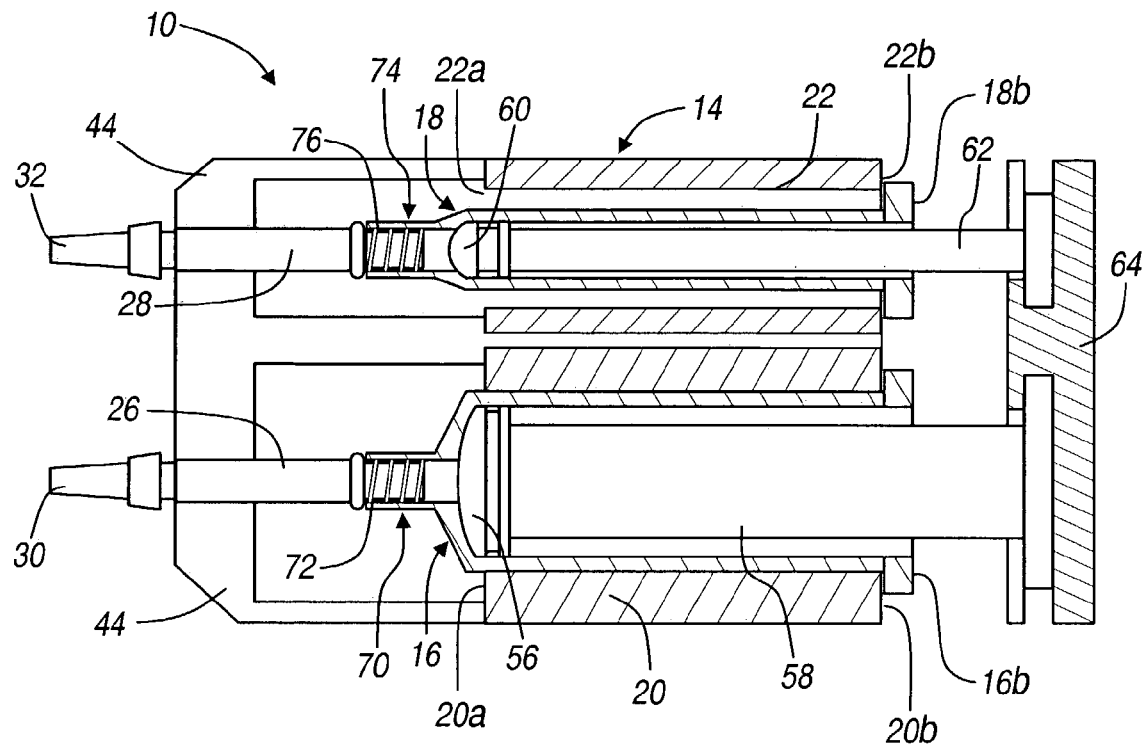
FIG. 3 is a top plan and partial cross-sectional view of the applicator of FIG. 1.

The cylinders 16 and 18 include expressing mechanisms or systems that may include activation members to express or disburse materials held therein at a selected time. With particular reference to FIG. 3, the first cylinder 16 includes a first piston 56 and a first piston rod 58. The second cylinder 18 also includes a second piston 60 and a second piston rod 62. The various pistons 56 and 60 in conjunction with the piston rods 58 and 62 may form various expressing members that form at least a portion of the expressing mechanism. Each of the piston rods 58 and 62 terminate in an actuation or depression member 64 that operably interconnects the first piston rod 58 and the second piston rod 62 to form a depression system. The depression member 64 may also be the third expressing member that interacts with the pistons 56 and 60 to form the expressing system. In this manner, the depression member 64 allows both of the piston rods 58 and 62 to be depressed at a substantially equal rate and substantially simultaneously. Although the depression member 64 is illustrated to substantially and permanently enclose the first cylinder rod 58 and the second cylinder rod 62, it will be understood that the depression member 64 may only be selectively affixed to the piston rods 58 and 62. In this manner, the depression member 64 may be removed from the piston rods 58 and 62 at a selected time. Moreover, this allows for a variation in the cylinders that are used with the applicator 10. As discussed above, the cylinders 16 and 18 may be syringes that are selectively coupled with the applicator 10. Therefore, at a selected time one of the cylinders 16 or 18 may be removed from the respective cylinder containing areas 20 or 22 and replaced with an alternative cylinder. At that time, the depression member 64 may be reattached to the remaining piston rod and the new piston rod to allow for actuation of the applicator 10.

The depression member 64 assists in defining a more complete expressing mechanism. This allows the volume of the first cylinder 16 and the second cylinder 18 to be evacuated substantially simultaneously. Moreover, the pistons 56 and 60 in the respective cylinders 16 and 18 are advanced at the same rate so that varying volumes are expressed from the respective cylinders 16 and 18 if the volume of the cylinders 16 and 18 differ. Nevertheless, it will be understood that the depression member 64 is not required and any appropriate means may be used to depress the various piston rods 58 and 62.

It will be understood, however, that if the first cylinder 16 and second cylinder 18 may not, and here illustrated do not have substantially equal volumes, the actual volume expressed out of the respective cylinders therefore, is not be equal. Rather, the distance that the respective pistons 56 and 60 travel along the length of the respective cylinders 16 and 18 may be equal, when depressing the single depression member 64, but the volume expressed is not.

The cylinder containing areas 20 and 22 extend substantially along the entire length of the respective cylinders 16 and 18. Specifically, the containing areas 20, 22 may be equi-distance to the cylinders 16 and 18. Nevertheless, it will be understood that the cylinders 16 and 18 may extend beyond the cylinder containing areas 20 and 22. Particularly, the cylinders 16 and 18 may extend towards the outlets 30 and 32 beyond a forward edge 20a of the first cylinder holder 20 and a forward edge 22a of the second cylinder holder 22.

Although the first cylinder 16 may extend beyond the forward end 20a of the first cylinder containing area 20 and the second cylinder 18 may extend beyond the forward end 22a of the second cylinder holding area 22, the cylinder containing areas 20 and 22 extend substantially to respective rearward ends 16b and 18b of the cylinders 16 and 18. The first cylinder holder 20 includes a back or rearward portion 20b which substantially engages or extends to a rear portion 16b of the first cylinder 16. Likewise, a rearward end or portion 22b of the second cylinder holder 22 extends to a rearward portion 18b of the second cylinder 18. Therefore, between the rearward end 16b of the first cylinder 16 and the rearward end 18b of the second cylinder 18, there is substantially no open space.

The cylinder containing portions 20 and 22 assist in expressing the material from the respective cylinders 16 and 18 by further supporting the cylinders 16 and 18 within the applicator 10. Specifically, as the single depression member 64 is depressed, the cylinders 16 and 18 are further pressed against the cylinder supporting portions 20 and 22. Therefore, additional support is provided to the cylinders 16 and 18 rather than simply the engagement between the cylinders 16 and 18 and the conduits 26 and 28.

The cylinders 16 and 18 may operably interconnect with the conduits 26 and 28 in any appropriate manner. According to the illustrated embodiment, the cylinder 16 includes a front or nose portion 70 which is operably engaged on a receiving end 72 of the first conduit 26. For example, the nose 70 includes internal threads which operably engage external threads on a receiving end 72 of the first conduit 26. Similarly, a nose portion 74 of the second cylinder 18 includes internal threads which operably engage a receiving end 76 of the second conduit 28. Therefore, a substantially liquid tight connection is formed between the cylinders 16 and 18 and the respective conduits 26 and 28.

Figure 2:
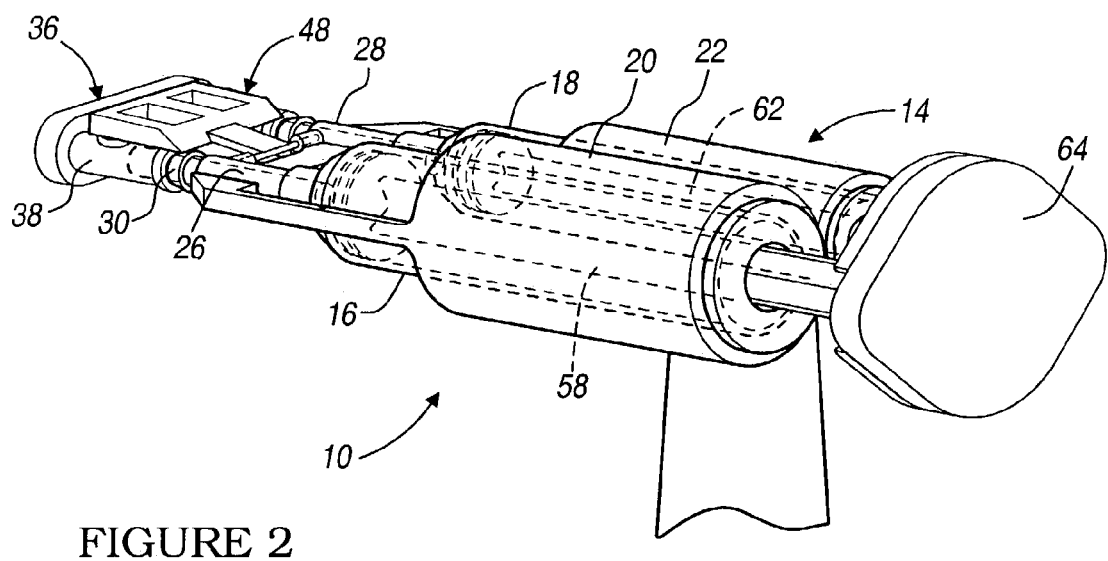
FIG. 2 is a perspective view of the applicator of FIG. 1 including an attachment affixed thereto.

With further reference to FIGS. 1 and 2, the handle 12 may be formed in any appropriate manner. For example, as illustrated, the handle 12 may include a gradual taper from a distal end 12a to a proximal end 12b. Generally, the proximal end 12b is fixed or formed integrally with the multi-component containing area 14. The handle 12 may be formed either between the cylinder containment areas 20 and 22 or substantially along either. Regardless, the handle 12 is positioned such that easy depression of the single depression member 64 is possible.

It will be understood that the handle 12 may also be formed in any other appropriate shape. For example, the handle 12 may be substantially cylindrical to allow easy grasping by a user. The handle 12 may also or rather include an appropriate texture to assist in grasping during use. The handle 12 may also include appropriate depressions, such as to receive the fingers of a user, to further assist in the use of the applicator 10.

The applicator 10 may interconnect with the spray attachment 36 or any other appropriate attachment. For example, the outlets 32 and 34 may be interconnected with a mixing conduit. Therefore, it will be understood that the applicator 10 is a substantially modular component such that any appropriate attachments may be affixed relative the outlets 30 and 32 of the applicator 10. The applicator 10 may also be used in a variety of applications and with a plurality of attachments. For example, the applicator may include a spray attachment including domes or guards that substantially surround spray tubes to further assist in deflection of the material towards the desired application area during use.

Figure 4:
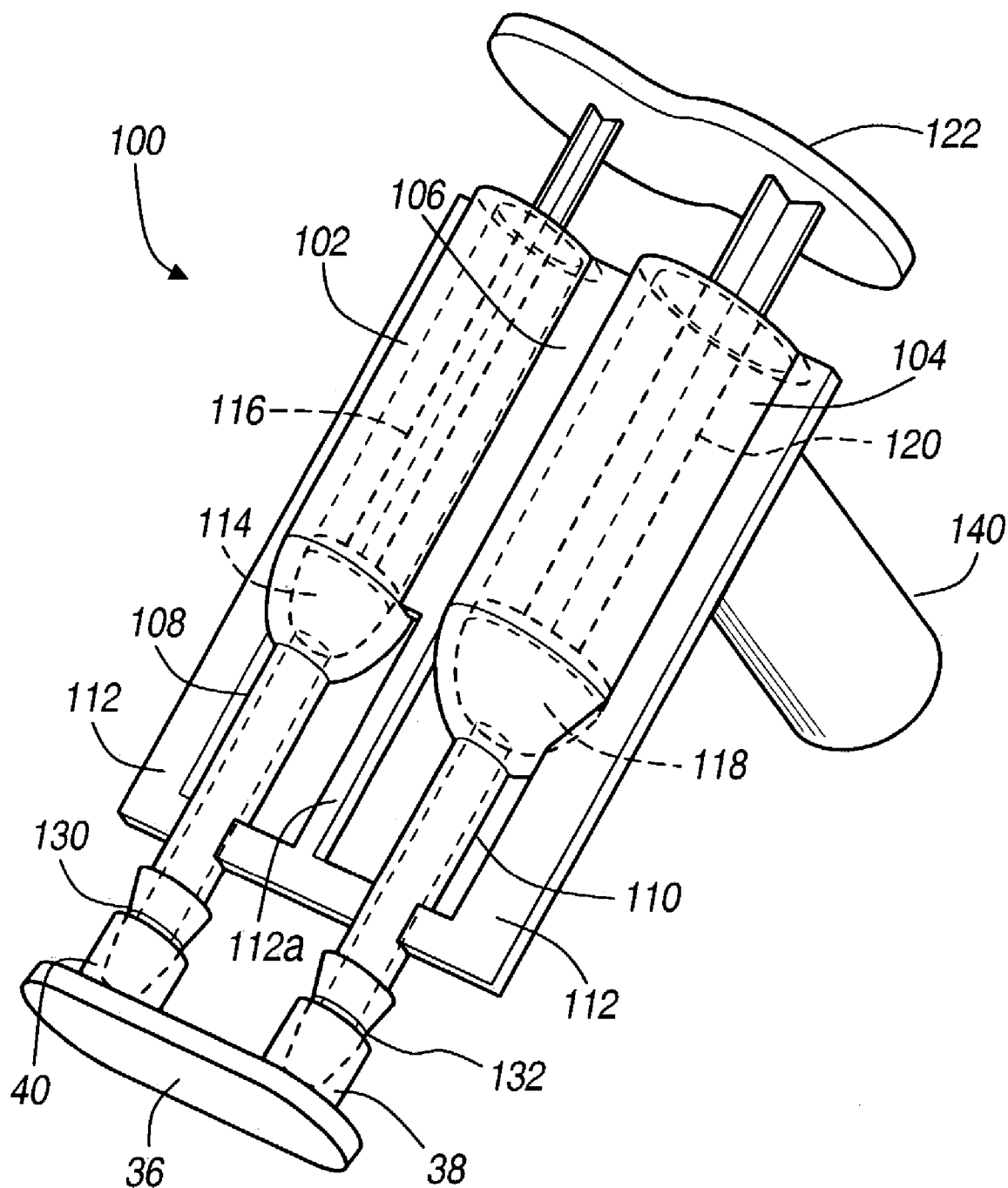
FIG. 4 is a perspective view of an applicator according to an alternative embodiment.

With reference to FIG. 4, an alternative applicator 100 is illustrated. The applicator 100 includes a first container or containing area 102 and a second container or containing area 104 interconnected such that the applicator 100 is substantially integral. Although interconnected through any appropriate structure, the first container 102 and second container 104 may be interconnected with an inter-web or support portion or member 106 extending substantially along the entire length of the containers 102 and 104 and is operable to interconnect the containers 102, 104 or portions holding the containers 102, 104. The first container 102 extends into a first conduit 108. The second container 104 extends into a second conduit 110. The respective conduits 108 and 110 may be substantially smaller in diameter than the respective containers 102 and 104. It will be understood, however, that the cross section of the containers 102 and 104 are substantially round. Nevertheless, the containers 102 and 104 may be any appropriate cross section. Similarly, the conduits 108 and 100 may be any appropriate shape.

According to the alternative embodiment of the applicator 100, the first container 102 is a substantially integrally formed with the first conduit 108. Moreover, the second container 104 is substantially integrally formed with the second conduit 110. Therefore, the containers 102 and 104 are not selectively or removably interconnected with the conduits 108 and 110, but rather substantially formed as a single piece or unit. In addition, the reinforcing web 106 is substantially integrally formed with the containers 102 and 104. Therefore, rather than providing a plurality of portions, the containers 102 and 104 including the conduits 108 and 110 and the supporting web 106 can be formed as a single piece. These various portions may then be formed simultaneously. For example, these portions may be injection molded as a single piece or cast and machined as a single piece.

Further support members 112 may extend from the cylinders 102 and 104 to interconnect and further stabilize the conduits 108 and 110. The support portion 112 may also include a center member 112a which extends to the other support portions 112 such that the conduits 108 and 110 are substantially stabilized and re-enforced for use. The support members 112 may also be integrally formed with the containers 102 and 104 and the conduits 108 and 110. Therefore, the main body of the applicator 100 may be formed as a single piece or unit at a single time.

The first and second containers 102 and 104 may contain a material that may expressed through the conduits 108 and 110. The first container 102 is substantially hollow and includes a first piston 114 disposed therein. Operatively connected to the first piston 114 is a first piston rod 116. Likewise, in the second cylinder 104 a second piston 118 is disposed therein and operatively connected to the second piston 118 is a second piston rod 120. The first and second piston rods 116 and 120 extend through a proximal end of the applicator 100 and terminate in a common depression member 122. The pistons 114, 118; rods 116, 120; common depression member 122 and other members, similar to the portions described above; may define an expressing system or mechanism and various members thereof.

The common depression member 122 operably interconnects the first piston rod 116 and the second piston rod 120. This allows, as described above, the first piston 114 and the second piston 118 to be advanced along the length of the first cylinder 102 and the second cylinder 104 in any substantially equal rate. Although, as discussed above, if the volume of the first cylinder 102 is not substantially equal to the volume of the second cylinder 104, the equal rate of advancement does not provide an equal volume being expressed from the respective cylinders 102 and 104. Nevertheless, appropriate volumes for the various cylinders 102 and 104 may be selected such that an appropriate or selected volume of material is expressed from each of the cylinders 102 and 104.

The conduits 108 and 110 terminate in appropriate outlets 130 and 132. The outlets 130 and 132 allow the attachment of an appropriate attachment such as the sprayer 36. The attachment portions 38 and 40 of the sprayer attachment 36 operably interconnect with the outlets 130 and 132 such that the material pushed out of the cylinders 102 and 104 may be expressed out the sprayer attachment 36. Although not specifically illustrated, it will be understood that a engagement member, such as the engagement member 48 illustrated in FIG. 1, may be included with the alternative applicator 100. For example, the engagement member may be hingedly attached with the support members 112 or the conduits 108 and 110 to operably engage the attachment 36 during use.

A handle or grasping member 140 extends from an appropriate portion of the applicator 100. For example, the handle 140 may extend from either the first container 102 or the second container 104. Alternatively, the handle 140 may extend from the center web 106. The handle 140 may otherwise be formed to span the reinforcement web 106 and interconnect with either the first or second container 102 or 104. Regardless, the handle 140 generally allows a user to hold the applicator 100, while being able to depress the single depression member 122 with a single hand. Therefore, the applicator 100 can be manipulated by a user with a single hand for ease of operation. It will also be understood that the handle 140 may be integrally formed with the portions, such as the containers 102 and 104 and the re-enforcing web 106. In this way, the entire applicator 100 may be formed simultaneously and substantially as a single piece. It will be understood, however, that the handle 140 may also be formed as a separate member and attached to an appropriate portion of the containers 102 or 104 or the web 106 to form the applicator 100.

The following discussion describes and illustrates a particular exemplary use of the applicator 10. Although specific reference to the applicator 10, including the removable or non-integral cylinders 16 and 18 will be described in detail, it will be understood that the applicator 100 having the integral cylinders 102 and 104 may also be used in the following manner. Likewise, although the following description describes a particular use for the applicators 10, 100, it is not meant to be a limiting example but merely one possible use for the applicators 10 and 100.

Returning to FIG. 1, the first cylinder 16 may be filled with a first component of a biological material. Similarly, the second cylinder 18 may be filled with a second biological component of a biological material. For example, the applicator 10 may be used to apply a biological adhesive including a mixture of thrombin and fibrinogen. Particularly, thrombin or fibrinogen may be filled into the first cylinder 16 while the other is filled into the second cylinder 18.

Depending upon the particular multi-component biological material to be applied with the applicator 10, varying volumes of the specific component may be desired. Because of varying volumes of the components may be desired, the volumes of the respective cylinders 16 and 18 may also be varied. For example, if the first cylinder has a greater volume than the second cylinder 18, the volume of material expressed from the first cylinder 16 as the single depression member 64 is depressed will be greater than the volume of material expressed from the second cylinder 18. In this manner, the volumes of the various components of the multi-component material may be selected and dependent upon the volume of the various cylinders.

Therefore, although the single depression member 64 may be depressed to advance the respective pistons 56 and 60 at an equal rate, a volume of material expressed from the first cylinder 16 may be different than a volume of material expressed from the second cylinder 18. It will be further understood that the volumes of the respective cylinders 16 and 18 can be selected such that the volume of material expressed as the respective pistons 56 and 60 are advanced is a selected volume of the respective material placed in the respective cylinders.

As supplied or during use, the applicator 10 may be in an unfilled state or in a filled state. If the applicator 10 reaches an unfilled state, the cylinders 16 and 18 may need to be filled with a material to allow the applicator 10 to later apply the material. If the cylinder 16 and 18 are individual syringes, they may be provided in a kit with the applicator 10. Therefore, the applicator system 10 is assembled after or during a surgical or medical procedure. In this example, therefore, the various syringes may be pre-filled with the selected material and simply placed into the cylinder container area 14. It will be understood, that although the following description describes a manner to fill the cylinder 16 and 18, a plurality of the cylinders 16 and 18 may be provided in the kit such that an emptied cylinder is simply discarded and replaced with a new filled cylinder. In the applicator 10, material may be transported through the first and second conduits 26 and 28 to the respective cylinders 16 and 18. The first conduit 26 defines a first cannula 26*a*. Similarly, the second conduit 28 defines a second cannula 28*a*. The first cannula 26*a* is operably interconnected with the interior of the first cylinder 16. Similarly, the second cannula 28*a* is operably interconnected with the interior of the second cylinder 18.

Figure 5:
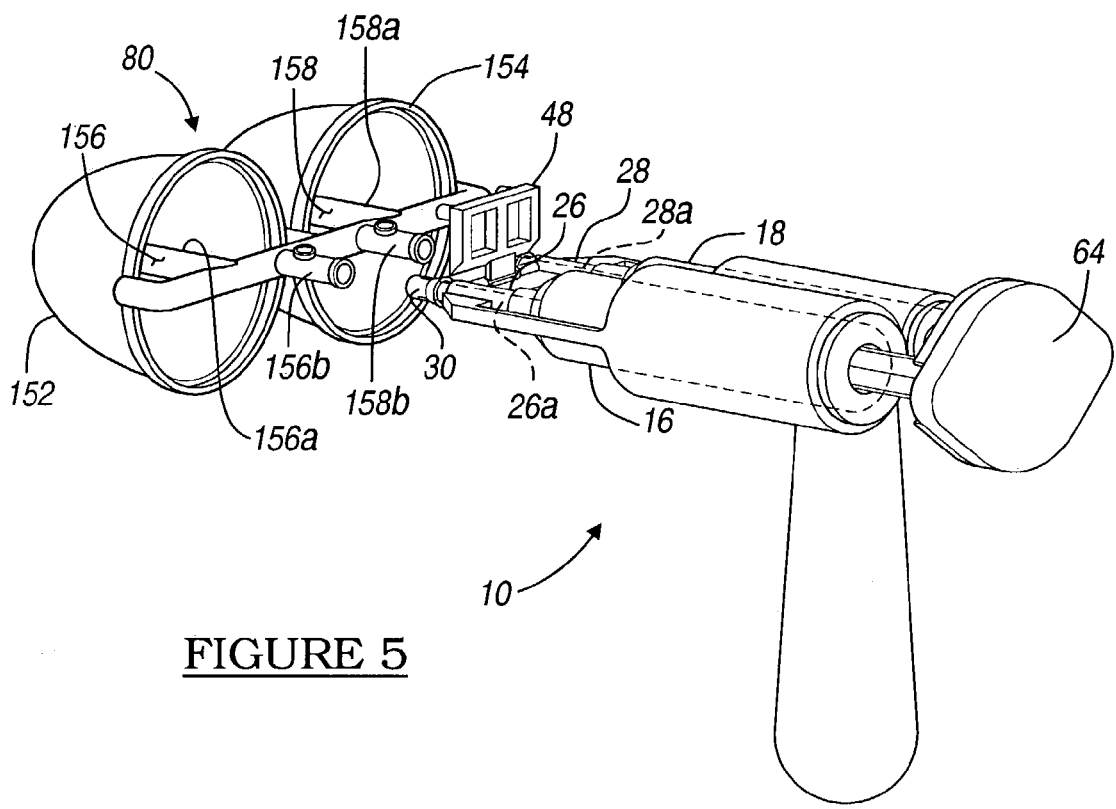
FIG. 5 is a perspective view of the applicator with filling containers according to an embodiment.

With reference to FIG. 5, a first exemplary method of filling the applicator 10 is illustrated. Because the first cannula 26*a* is operably connected to the interior of the first cylinder 16 and the second cannula 28*a* is operably connected to the interior of the second cylinder 18, material may be passed through the conduits 26 and 28 to the interior of the cylinder 16 and 18. When material is introduced into the cylinders 16 and 18 through the conduits 26 and 28 the outlets 30 and 32 effectively become "inlets" for the filling procedure.

A filling station 150 may be supplied which includes a first filling bucket or container 152 and a second filling bucket or container 154. Operably connected to the first filling container 152 is a first filling conduit 156. The first filling conduit 156 includes a inlet end 156*a* and an outlet end 156*b*. Similarly, the second bucket 154 includes a second filling conduit 158 which includes an inlet end 158*a* and an outlet end 158*b*. The first outlet end 156*b* operably interconnects with the first inlet 30. Similarly, the second outlet 158*b* is operably connected to the second inlet 32. Once the connections are made between the bucket outlets 156*b* and 158*b* and the inlets of the applicator 30 and 32, the cylinder 16 and 18 may be filled. According to this illustration, the single depression member 64 may be pulled out from the cylinders thereby forming a vacuum therein. In this manner, the material from the filling station 150 is pushed into the respective cylinders 16 and 18.

It will be understood that the filling buckets 152 and 154 may be closed and coded such that the appropriate material is filled into the appropriate one of the cylinders 16 and 18. This is particularly important when a varying volume of material is required to be applied. Nevertheless, according to the embodiment with the filling station 150, no additional or exterior power sources are required to fill the applicator 10. Simply, the vacuum created within the cylinder 16 and 18 is the only power necessary to fill the respective cylinders 16 and 18.

Figure 6:
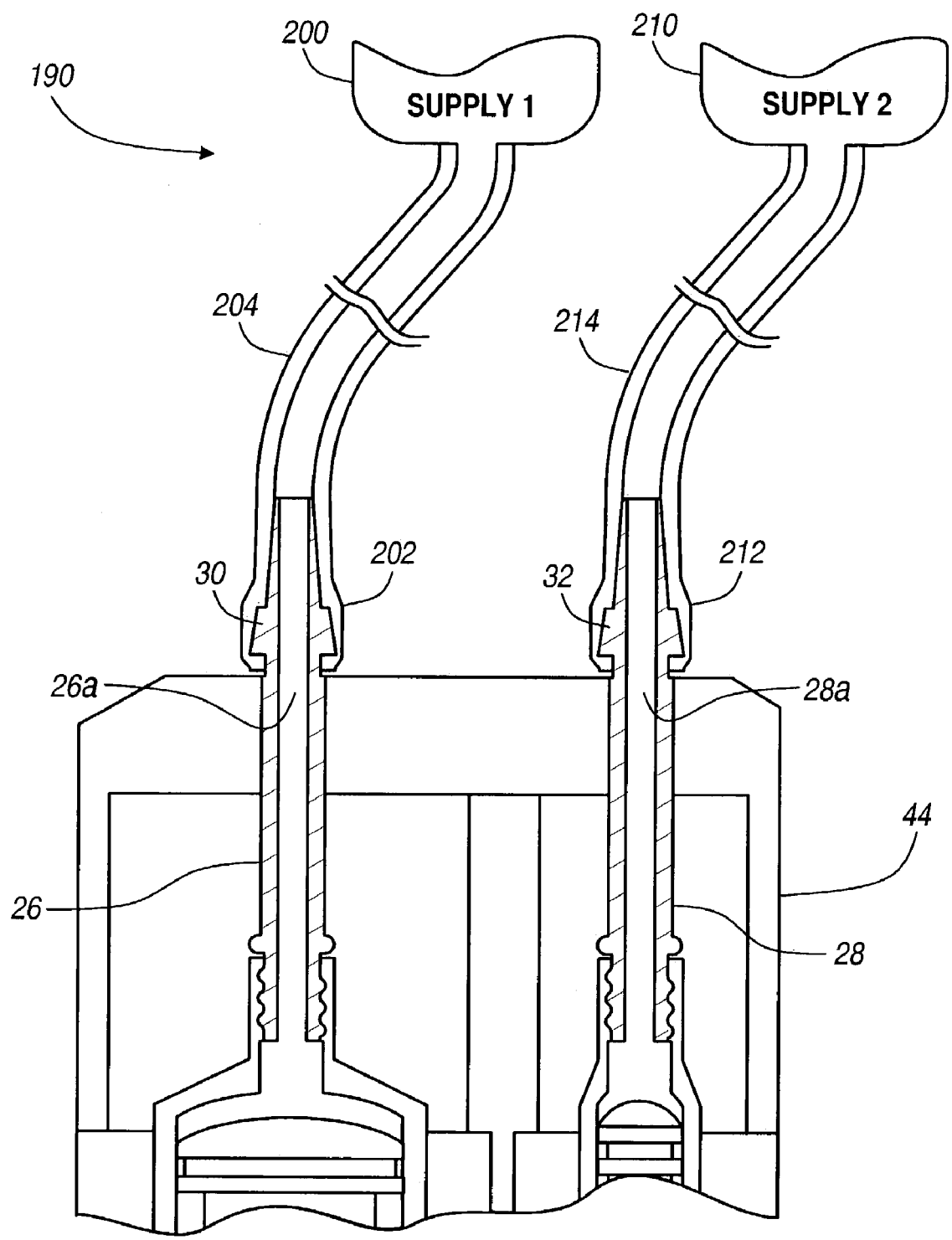
FIG. 6 is a detailed view of an alternative filling mechanism.

With reference to FIG. 6, a second filling embodiment includes a filling station 190. The filling station 190 includes a first supply 200 which is interconnected with the first inlet 30 with a first connector 202. A first supply conduit 204 operably interconnects the first supply 200 and the connector 202. Similarly, a second supply 210 is operably interconnected with the second outlet 32 through a second connector 212. In this way, a second material may be supplied through a second supply line 214 through the second cannula 28*a*. Again, in this case, the second outlet 32 actually becomes an inlet to allow material to be supplied to the second cylinder 18 through the second cannula 28*a*.

The supplies 200 and 210 include the materials to be drawn into the respective cylinders 16 and 18. During the filling procedure, the single depression member 64 may be pulled away from the cylinders 16 and 18 thereby pulling on the first and second piston rods 58 and 62 thereby pulling the pistons 56 and 60. Pulling the pistons 56 and 60 away from the outlets 30 and 32 produces a vacuum within the respective cylinders 16 and 18. This vacuum allows the materials from the respective supplies 200 and 210 to be pushed into or drawn into the respective cylinders 16 and 18. Therefore, the material can be filled into the cylinders 16 and 18 from the respective supplies 200 and 210 without any additional assistance.

Nevertheless, it will be understood that the supplies 200 and 210 may be pressurized or otherwise powered such that material is brought from the supplies 200, 210 into the respective cylinders 16 and 18. For example, a pump may be interconnected between the supply 200 and the connector 202 and also between the supply 210 and the connector 212 to pump the material from the respective supplies 200, 210 into the cylinders 16, 18. In this manner, the cylinders 16, 18 may be filled without a manual operation by a user other than operating the pump. Similarly, if the supplies 200, 210 are pressurized, a valve may be disposed between the supply 200, 210 and a respective connector 202 and 212 such that when the valve is opened, material is pushed from the supplies 200, 210 into the respective cylinders 16 and 18. It will be understood that the integral cylinders 102 and 104 of the applicator 100 may also be filled in a similar manner.

After the first and second cylinders 16 and 18 are filled with the appropriate materials, materials may be expressed from the cylinders 16 and 18 to a desired application area. In one use, the connectors 202 and 212 are removed from the outlets 30 and 32 and the spray applicator 36 operably interconnected therewith. At this point, the single depression member 64 may be depressed such that the material supplied within the cylinders 16 and 18 is expressed through the spray applicator 36 as the pistons 56 and 60 are pushed through the cylinders 16 and 18. As the material is expressed out the cannula 26*a* and 28*a*, the material is forced through the spray attachment 36 and sprayed onto a desired area. The material may be continually expressed through the respective cannula 26*a* and 28*a* until the respective cylinders 16 and 18 are depleted of the supplied material.

After the cylinders 16 and 18 are depleted of the supplied material, the cylinders 16 and 18 may be refilled through the cannula 26*a* and 28*a* as described above. Therefore, the applicator 10 may be used for more than one application of the material placed within the cylinders 16 and 18. Similarly, the cylinders 16 and 18 may be emptied by depressing on the single depression member 64 through any appropriate attachment or through the outlets 30 and 32. Because the cylinders 16 and 18 may be filled by attaching them to respective supplies 200 and 210 to refill the cylinders 16 and 18 the applicator 10 may be used a plurality of times in a single procedure or may be cleaned and sterilized for use in a plurality of procedures.

Any number of attachments may be used to interconnect with the outlets 30 and 32. Rather than providing the spray attachment 36, a tube or mixing conduit or cannula attachment may be affixed thereto. Therefore, the material may be provided as a bead rather than a mist to be applied to a particular or selected area.

In addition, the applicator 10, including the cylinder engaging portions 20 and 22 may be sized in any appropriate manner to receive any selected cylinders 16 and 18. For example, the area within the cylinder containing areas 20 and 22 may be substantially the same and the cylinders placed in the areas having portions that engages the rear portions 20b and 22b rather than simply compressing the conduit engagement portions 72 and 74. Therefore, the volume of the cylinders 16 and 18 may be changed and selected for a particular use or application of materials. Rather than having a substantially integral device which can only provide materials in one rate, the cylinders 16 and 18 may be interchanged such that varying volumes of material may be supplied at particular times. In this way, the applicator 10 may be used to supply a bio-adhesive including the materials of fibrinogen and thrombin or providing an adhesive which includes a different multi-component bio material which must be supplied at a rate different than the thrombin and fibrinogen to form an appropriate seal or adhesive.

The above description is merely exemplary in nature and, thus, variations that do not depart from the gist are intended to be within the scope of the following claims. Such variations are not to be regarded as a departure from the spirit and scope of the following claims.

What is claimed is:

1. An applicator for applying a multi-component biomaterial, comprising:
   a first container extending along a first axis to selectively contain and disburse a first component;
   a second container extending along a second axis to selectively contain and disburse a second component;
   a container holder operable to hold and orient said first container and said second container and a pistol grip handle graspable by a user;
   a first conduit extending along said first axis and immediately from said first container; and
   a second conduit extending along said second axis and immediately from said second container;
   wherein the first component disposed in said first container is expressed through said first conduit; and
   wherein the second component disposed in said second container is expressed through said second conduit.

2. The applicator of claim 1, further comprising:
   a first activation member associated with said first container; and
   a second activation member associated with said second container.

3. The applicator of claim 2, wherein:
   said first activation member includes a piston and a piston rod extending along said first axis; and
   said second activation member includes a second piston and a second piston rod extending along said second axis.

4. The applicator of claim 2, wherein a single manual depression member operably interconnects said first activation member and said second activation member.

5. The applicator of claim 1, wherein said container holder includes:
   a first engaging portion to engage said first container;
   a second engaging portion to engage said second container; and
   a member extending between said first container engagement portion and said second container engagement portion.

6. The applicator of claim 1, further comprising:
   a reinforcement member extending between said container holder and said conduits;
   wherein said reinforcement member stabilizes and maintains said first conduit end said second conduit in a selected orientation.

7. The applicator of claim 1,
   wherein the pistol grip handle extends at an angle from said container holder.

8. The applicator of claim 7, wherein said handle is formed as a portion of and extending from said container holder in a selected orientation to assist in use of the applicator.

9. The applicator of claim 7, further comprising:
   a depression system;
   wherein said graspable member allows the applicator to be operated by a single hand of a user such that the user is able to grasp the graspable member and directly depress the depression system at a selected time with a single hand.

10. The applicator of claim 1, further comprising:
    a first outlet extending from said first conduit; and
    a second outlet extending from said second conduit.

11. The applicator of claim 10, further comprising:
    an attachment to be selectively attached to said first outlet and said second outlet;
    wherein the first component contained in said first container and the second component contained in said second container is expressed through said attachment at a selected time.

12. The applicator of claim 11, wherein said attachment includes an atomizer so that when material is expressed from said first container and said second container the material is substantially atomized after passing therethrough.

13. The applicator of claim 1, further comprising:
    an expressing system including a first piston and a first piston rod operably associated with said first container;
    a second piston and a second piston rod operably associated with said second container; and
    a graspable member operably extending from said container holder;
    wherein said first piston and first piston rod and said second piston and second piston rod are oriented such that a user may grasp the graspable member and directly depress said first piston rod and said second piston rod substantially simultaneously.

14. The applicator of claim 1, wherein:
    said first container defines a first volume;
    said second container defines a second volume that differs from said first volume.

15. The applicator of claim 1, wherein:
    said first container includes a conduit engaging portion defining internal threads;
    said second container defines a second conduit engaging portion defining internal threads;

said first conduit defines a container engaging portion defining exterior threads, wherein the interior threads of the first conduit engaging portion operably engages said threads of said first container engaging portion;

said second conduit defines a second container engaging portion defining exterior threads, wherein the interior threads of the second conduit engaging portion operably engages said threads of said second container engaging portion;

wherein said first container is selectively affixed to said first conduit and said second container is selectively affixed to said second conduit.

16. The applicator of claim 1, wherein said first container selectively defines a first volume and selectively engages said container holder;

said second container selectively defines a second volume and selectively engages said second conduit.

17. An applicator for applying at least one component of a multi-component bio material, comprising:

a single member comprising a first container extending along a first axis and a second container extending along a second axis;

a first conduit integrally formed with said first container and extending along said first axis; and a second conduit formed substantially integrally with said second container and extending along said second axis;

a graspable member operably associated with said first container, said second container; and an expressing member to express material from said first container, said second container, or both;

wherein said first container contains a first biological material and said second container containing a second material may each simultaneously express the respective materials at a selected time;

wherein the first material contained within said first container is expressed through said first conduit and the second material contained within said second container is expressed through said second conduit;

wherein said graspable member and said expressing member are associated with said first container and said second container such that material disposed within said first container and said second container is selectively expressed substantially simultaneously.

18. The applicator of claim 17, further comprising:

a first outlet extending distally from said first conduit; and:

a second outlet extending distally from said second conduit;

wherein material expressed from said first container is expressed through said first outlet and material expressed from said second container is expressed through said second outlet.

19. The applicator of claim 17, further comprising:

a graspable member operably associated with said first container and said second container;

wherein material within said first container and said second container may be expressed using only a single hand.

20. The applicator of claim 17, further comprising:

a first expressing member operably associated with said first container such that said first expressing member allows for selected expressing of the first material disposed in said first container; and a second expressing member operably associated with said second container such that the second material disposed in said second container is selectively expressible from said second container.

21. The applicator of claim 20, further comprising:

a third expressing member operably interconnecting said first expressing member and said second expressing member such that said first expressing member and said second expressing member are operable to express material from said first container and said second container substantially simultaneously.

22. The applicator of claim 21, wherein said first expressing member, said second expressing member, and said third expressing member are integrally formed as a single member.

23. The applicator of claim 17, wherein:

said first container defines a first volume and said second container defines a second volume;

said first volume differs from said second volume.

24. A method of applying a multi-component bio-material to a selected area and at a selected volume with an applicator including a containing area for each of the components of the multi-component material, wherein the applicator includes a conduit acting as an outlet and an inlet for the respective containers, the method comprising:

supplying at least a first material to a first container and a second material to a second container, wherein supplying the material includes:

interconnecting a first supply with said first container through a first conduit;

interconnecting a second supply with said second container through a second conduit;

filling said first and second container with material from said first and second supply;

interconnecting said first supply with said first container by providing a first connector operable to connect to said first conduit, and providing a supply line a between the said first supply and said first connector; and interconnecting said second supply with said second container by providing a second connector operable to connect to said second conduit, and providing a supply line between the said second supply and said second connector;

supplying a graspable member operably associated with said first container and said second container to allow easy expressing of the first material from said first container and the second material from said second container, wherein the graspable member is a pistol grip; and selectively expressing the material from the first and second containers substantially simultaneously to a selected area;

wherein the material may be selectively supplied at a selected rate from each of said first and second containers.

25. The method of claim 24, further comprising:

disposing a first piston in said first container and disposing a second piston in said second container;

wherein filling said first and second containers includes;

forming a vacuum in said first container by moving said first piston and forming a vacuum in said second container by moving said second piston to evacuate a selected volume of said first and second containers.

26. The method of claim 24, wherein filling said first and second containers includes pressurizing said first and second supplies such that material is forced from said first and second supplies into said first and second containers.

27. The method of claim 24, wherein filling said first and second containers includes:

disposing a first pump operable to move material disposed in said first supply to said first container;

disposing a second pump operable to move material disposed in said second supply to said second container; and operating said first and second pumps to pump material within said first and second supplies to the respective first and second containers.

28. The method of claim 24, wherein expressing the material from said first container and said second container includes:

expressing the material through said first conduit from said first container and expressing the material from said second container through said second conduit.

29. The method of claim 24, wherein expressing the material from said first container and said second container includes:

depressing a first piston disposed in said first container and a second piston disposed in said second container substantially simultaneously such that materials contained within said first container and said second container are expressed substantially simultaneously.

30. The method of claim 24, further comprising:

grasping the applicator with a first hand of a user; and depressing a first piston disposed in said first container and depressing a second piston disposed in a second container with the first hand of the user.

31. The method of claim 24, further comprising:

selecting said first container to have a first volume; and selecting said second container to have a second volume.

32. The method of claim 31, wherein said first volume and said second volume differ.

33. An applicator for applying a multi-component biomaterial, comprising:

a first container extending along a first axis operable to selectively contain and express a first component;

a second container extending along a second axis operable to selectively contain and express a second component;

a container holder operable to hold and orient said first container and said second container;

a direct expressing system operable to allow the substantially simultaneous expression of the first component and the second component upon receiving direct engagement from a user; and a graspable member extending a distance along a third axis that is different than the first axis or the second axis and from said container holder;

wherein a user is able to grasp said graspable member with a first hand and engage said expressing system with the first hand.

* * * * *